(12) United States Patent
Endo et al.

(10) Patent No.: US 10,393,694 B2
(45) Date of Patent: Aug. 27, 2019

(54) GAS SENSOR

(71) Applicant: DENSO CORPORATION, Kariya, Aichi-pref. (JP)

(72) Inventors: Yuusuke Endo, Yokkaichi (JP); Takashi Araki, Nagoya (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 14/646,137

(22) PCT Filed: Nov. 18, 2013

(86) PCT No.: PCT/JP2013/081017
§ 371 (c)(1),
(2) Date: May 20, 2015

(87) PCT Pub. No.: WO2014/080859
PCT Pub. Date: May 30, 2014

(65) Prior Publication Data
US 2015/0300979 A1 Oct. 22, 2015

(30) Foreign Application Priority Data

Nov. 20, 2012 (JP) .................. 2012-254228
Sep. 25, 2013 (JP) .................. 2013-198541

(51) Int. Cl.
*G01N 27/407* (2006.01)
*G01M 15/10* (2006.01)
*G01N 33/00* (2006.01)

(52) U.S. Cl.
CPC ...... *G01N 27/4077* (2013.01); *G01M 15/102* (2013.01); *G01N 33/0009* (2013.01)

(58) Field of Classification Search
CPC .......... G01N 27/4077; G01N 33/0009; G01M 15/102
See application file for complete search history.

(56) References Cited

U.S. PATENT DOCUMENTS

| 5,238,552 A | 8/1993 | Kato et al. |
| 5,341,788 A | 8/1994 | Uchida |

(Continued)

FOREIGN PATENT DOCUMENTS

| JP | 63-78265 | 5/1988 |
| JP | 1-146155 | 10/1989 |

(Continued)

OTHER PUBLICATIONS

International Search Report (8 pages) dated Feb. 18, 2014, issued in PCT/JP2013/081017 and English translation (1 page).
Written Opinion (4 pages) dated Feb. 18, 2014, issued in PCT/JP2013/081017 and English translation (10 pages).

*Primary Examiner* — J. Christopher Ball
(74) *Attorney, Agent, or Firm* — Nixon & Vanderhye P.C.

(57) ABSTRACT

A gas sensor 1 includes a sensor element 2, a housing 13 and an element cover 3. The sensor element 2 is provided with a gas introduction part 271 for introducing a measurement gas thereinto at a distal end portion 201 thereof. The element cover 3 includes an inner cover 4 disposed so as to cover the distal end portion 201 of the sensor element 2 and an outer cover disposed outside the inner cover 4. The outer cover 5 is provided with outer inlet openings 52 for introducing the measurement gas into the outer cover 5. The inner cover 4 is provided with inner inlet openings 42 for introducing the measurement gas into the inner cover 4. The axial intermediate position C1 of the gas introduction part 271 of the sensor element 2 is more to the axial proximal end side X2 than the axial proximal end position D1 of the inner inlet opening 42 of the inner cover 4.

17 Claims, 11 Drawing Sheets

(56) References Cited

U.S. PATENT DOCUMENTS

| | | |
|---|---|---|
| 6,279,376 B1 * | 8/2001 | Yamada ............ G01N 27/4077 73/23.2 |
| 6,346,179 B1 | 2/2002 | Makino et al. |
| 6,348,141 B1 | 2/2002 | Kato et al. |
| 2005/0178187 A1 | 8/2005 | Nakagawa |
| 2007/0113617 A1 | 5/2007 | Yamauchi |
| 2007/0251823 A1 | 11/2007 | Yamada |
| 2008/0028831 A1 | 2/2008 | Nakashima et al. |
| 2009/0020425 A1 | 1/2009 | Yamada |
| 2009/0126349 A1 | 5/2009 | Shimomura et al. |
| 2010/0155240 A1 * | 6/2010 | Matsuoka .......... G01N 27/4077 204/424 |
| 2010/0225339 A1 | 9/2010 | Fujita |
| 2012/0145543 A1 | 6/2012 | Sugaya et al. |
| 2015/0276654 A1 | 10/2015 | Araki |

FOREIGN PATENT DOCUMENTS

| | | |
|---|---|---|
| JP | 11-248671 | 9/1999 |
| JP | 2000-220489 | 8/2000 |
| JP | 2003-43002 | 2/2003 |
| JP | 2007-101353 | 4/2007 |
| JP | 2008-058297 | 3/2008 |
| JP | 2009-025076 | 2/2009 |
| JP | 2010-185871 | 8/2010 |
| JP | 2012-21895 | 2/2012 |
| JP | 2012-177380 | 9/2012 |
| JP | 2012-211858 | 11/2012 |
| JP | 2013-117381 | 6/2013 |
| JP | 2014-122876 | 7/2014 |

* cited by examiner

GAS SENSOR

This application is the U.S. national phase of International Application No. PCT/JP2013/081017 filed 18 Nov. 2013 which designated the U.S. and claims priority to JP Patent Application No. 2012-254228 filed 20 Nov. 2012 and JP Patent Application No. 2013-198541 filed 25 Sep. 2013, the entire contents of each of which are hereby incorporated by reference.

TECHNICAL FIELD

The present invention relates to a gas sensor for detecting a concentration of a specific gas contained in a measurement gas.

BACKGROUND ART

Conventionally, there are known gas sensors to be mounted on an exhaust pipe of an internal combustion engine or the like of a vehicle for detecting a concentration of a specific gas contained in an exhaust gas as a measurement gas. The gas sensors include ones which include a sensor element that detects a specific gas concentration contained in a measurement gas, a housing holding the sensor element inserted thereinto, and an element cover disposed on the distal end side of the housing.

For example, patent document 1 discloses a gas sensor provided with a double-structured element cover for preventing a sensor element from being flooded and so on, the double-structured element cover including an inner cover for covering a distal end portion of the sensor element provided with a gas inlet part, and an outer cover disposed outside the inner cover. The outer cover of this gas sensor is provided with outer inlet openings for introducing a measurement gas into the outer cover.

CITATION LIST

Patent Literature

[PTL1] Japanese Patent Application Laid-open No. 2009-25076

SUMMARY OF INVENTION

Technical Problem

In a multi-cylinder internal combustion engine, there arises a cylinder-to-cylinder air/fuel ratio variation (inter-cylinder imbalance) among their cylinders. In recent years, it is required to accurately detect the inter-cylinder imbalance with a gas sensor to perform air/fuel ratio control for the respective cylinders of an internal combustion engine by further exhaust gas regulations and fuel economy regulations. Accordingly, it is necessary to further increase the responsiveness of the gas sensor to air/fuel ratio change for the respective cylinders in order to more accurately detect change of the output value (air/fuel ratio: A/F) of the gas sensor as an index of the inter-cylinder imbalance. More specifically, other than increasing the responsiveness of the gas sensor to A/F change, it is imperative that, particularly in the element cover for protecting the sensor element, a measurement gas is caused to reach the gas detecting part (a part for detecting the measurement gas) of the sensor element as much as possible quickly through a short distance, and measurement gases having different A/Fs successively discharged from the respective cylinders are made difficult to mix with one another.

However, since the gas sensor described in the above patent document 1 attaches importance to preventing the sensor element from being flooded, its responsiveness to the detection of the inter-cylinder imbalance is not sufficient to accurately detect the inter-cylinder imbalance of an internal combustion engine. The cause of this is considered to be that the distance which the measurement gas introduced from the inner inlet openings into the inner cover travels to reach the gas introduction part of the sensor element is large. If this distance is large, the measurement gases discharged in succession and reaching the gas detection part of the sensor element in succession are likely to mix with one another. If the measurement gases mix with one another, it results in that, when the air/fuel ratio of the measurement gas discharged from one of the cylinders has been shifted to the rich side and the air/fuel ratio of the measurement gas discharged from another one of the cylinders has been shifted to the lean side, an air/fuel ratio of a mix of these gases is detected. In this case, there is a concern that the accuracy of detection of the inter-cylinder imbalance is lowered, causing the responsiveness of the gas sensor to be lowered.

The present invention has been made in view of such background with an object to provide a gas sensor capable of increasing the accuracy of detection of the inter-cylinder imbalance of an internal combustion engine, and is excellent in the responsiveness to the detection of the inter-cylinder imbalance.

Solution to Problem

One aspect of the present invention is in a gas sensor that includes:

a sensor element for detecting a concentration of a specific gas contained in a measurement gas;

a housing holding the sensor element inserted thereinto; and an element cover disposed at an axial distal end side of the housing, wherein the sensor element is provided with a gas introducing part for introducing the measurement gas thereinto at a distal end portion thereof;

the element cover includes an inner cover disposed so as to cover the distal end portion of the sensor element and an outer cover disposed outside the inner cover, the outer cover is provided with an outer inlet opening for introducing the measurement gas into the outer cover, the inner cover is provided with an inner inlet opening for introducing the measurement gas into the inner cover, and an axial intermediate position of the gas introduction part of the sensor element is more to an axial proximal end side than an axial proximal end position of the inner inlet opening of the inner cover is.

Advantageous Effect of the Invention

In the above gas sensor, the distal end portion of the sensor element is provided with the gas introduction part for introducing the measurement gas thereinto. The inner cover covering the distal end portion of the sensor element is provided with the inner inlet opening for introducing the measurement gas into the inner cover. The axial intermediate position of the gas introduction part of the sensor element is more to the axial proximal end side than the axial proximal end position of the inner inlet opening of the inner cover is.

That is, the measurement gas introduced into the outer cover (between the outer cover and the inner cover) from the outer inlet opening is introduced into the inner cover from the inner inlet opening, and reaches the gas introduction part of the sensor element. The inventors of the present invention found that, in such a stream of the measurement gas, the distance which the measurement gas introduced into the inner cover from the inner inlet opening travels to reach the gas introduction part of the sensor element greatly contributes to the accuracy of detection of the inter-cylinder imbalance of an internal combustion engine and the responsiveness of the detection of the inter-cylinder imbalance.

Also, the inventors of the present invention found that, to shorten the distance which the measurement gas introduced from the inner inlet opening into the inner cover travels to reach the gas introduction part of the sensor element, it is very advantageous to make the axial proximal end position of the inner inlet opening from which the measurement gas is introduced into the inner cover is more to the axial proximal end side than the axial intermediate position of the gas introduction part from which the measurement gas is introduced into the inside of the sensor element is.

Accordingly, the measurement gas introduced into the inner cover from the inner inlet opening can be caused to reach the gas introduction part of the sensor element quickly through a distance as short as possible. Further, the measurement gas can be caused to reach the gas introduction part of the sensor element without mixing with the measurement gas introduced from another inner inlet opening. Further, the measurement gases of the respective cylinders of an internal combustion engine can be caused to reach the gas introduction part of the sensor element in succession, to suppress the measurement gases of the respective cylinders from mixing with one another before reaching the gas introduction part of the sensor element.

As a result, the responsiveness of the gas sensor can be increased to thereby more accurately detect the output value (air/fuel ratio A/F and so on, for example) which provides an index of the inter-cylinder imbalance of the internal combustion engine. Thus, the accuracy of the detection of the inter-cylinder imbalance of the internal combustion engine can be increased.

In this manner, the accuracy of detection of the inter-cylinder imbalance of an internal combustion engine can be increased, and a gas sensor excellent in the responsiveness to the detection of the inter-cylinder imbalance can be provided.

DESCRIPTION OF EMBODIMENTS

Figure 1:
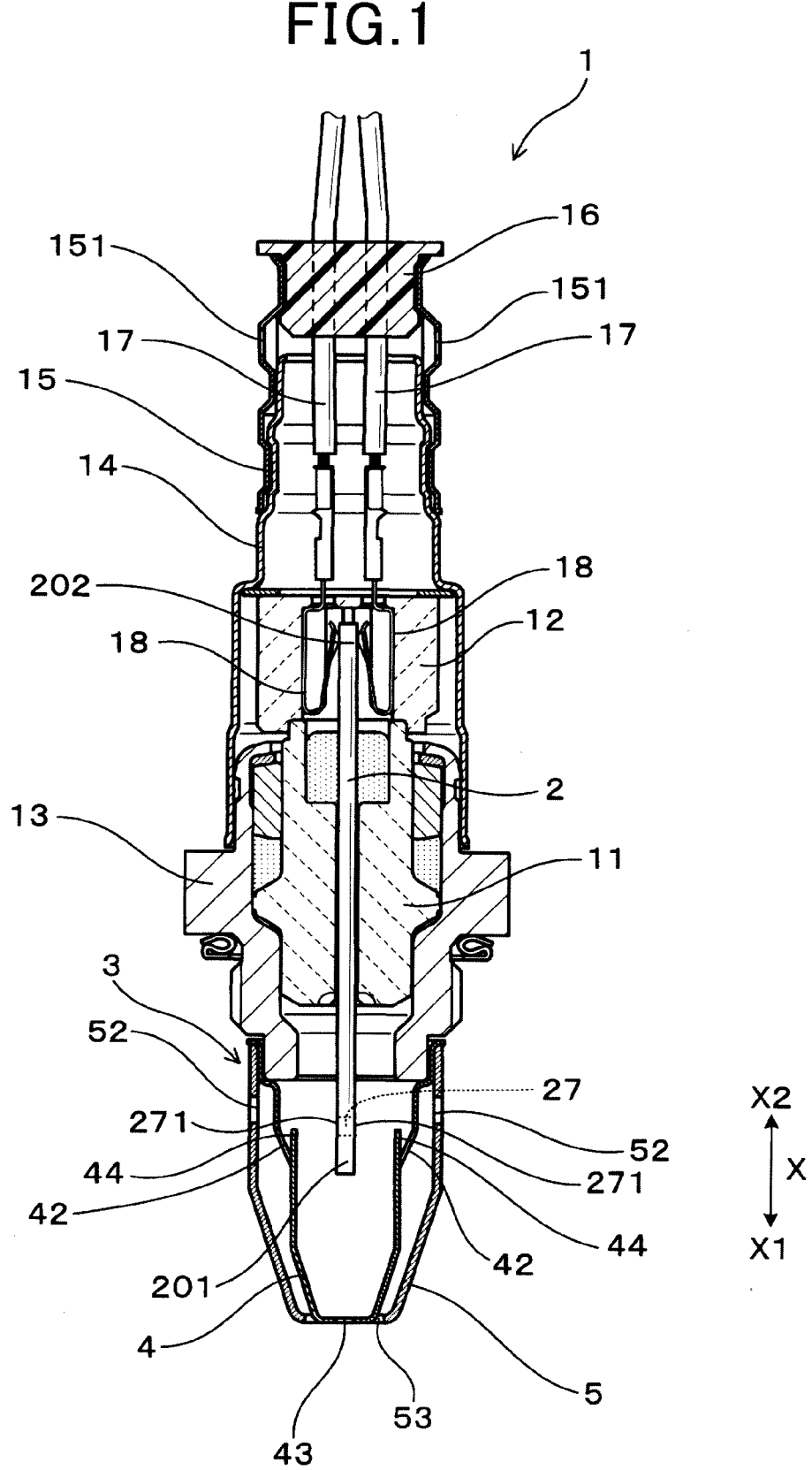
FIG. 1 is a cross-sectional explanatory view showing an overall structure of a gas sensor according to a first embodiment of the invention.

In the gas sensor, the words "axial distal end side" means one axial end side of the gas sensor, or the side at which the gas sensor is exposed to the measurement gas. The words "axial proximal end side" means the side opposite to it.

As the sensor element, it is possible to use a stacked sensor element formed by stacking an oxygen ion-conductive solid electrolyte body provided with a measurement gas-side electrode and a reference gas-side electrode, a diffusion resistance layer which allows the measurement gas to transmit therethrough to contact with the measurement gas-side electrode and so forth, for example. In this configuration, part of the diffusion resistance layer is exposed to the outer surface of the sensor element, the exposed part making the gas introduction part.

The gas introduction part may be provided at a plurality of positions in the distal end portion of the sensor element. A protection layer or the like may be provided on the outer surface of the sensor element so as to cover at least the exposed part (gas introduction part) of the diffusion resistance layer to trap poisoning components in the measurement gas.

In the outer cover, the outer inlet opening may be provided plurally side by side in the circumferential direction. In the inner cover, the inner inlet opening may be provided plurally side by side in the circumferential direction. In a case where the inner inlet opening is provided plurally, it is preferable that the axial intermediate position of the gas introduction part of the sensor element is more to the axial proximal end side than the axial proximal end positions of all the inner inlet openings are.

In the case where the inner inlet opening is provided plurally, it is preferable that the axial positions of all the inner inlet openings are the same. Also, it is preferable that the radial distances from the inner inlet openings to the gas introduction part are the same. In this case, the variation among the distances from the inner inlet openings to the gas introduction part of the sensor element can be suppressed to further increase the accuracy of detection of the inter-cylinder imbalance of an internal combustion engine and the responsiveness to the detection of the inter-cylinder imbalance.

When the axial distance from the axial proximal end position of the inner inlet opening to the axial intermediate position of the gas introduction part of the sensor element is a, 0 mm<a≤3.0 mm preferably, and more preferably, 0.7 m≤a≤3.0 mm. In this case, it is possible to cause the measurement gas introduced into the inner cover from the inner inlet opening to reach the gas introduction part of the sensor element quickly through a further shorter distance. As a result, the accuracy of detection of the inter-cylinder imbalance of an internal combustion engine and the responsiveness to the detection of the inter-cylinder imbalance can be further increased.

When the axial distance a between the axial intermediate position of the gas introduction part of the sensor element and the axial proximal end position of the inner inlet opening of the inner cover is smaller than or equal to 0 mm, or larger than 3 mm, there is a concern that the distance which the measurement gas introduced into the inner cover from the inner inlet opening travels to reach the gas introduction part of the sensor element becomes long, causing the responsiveness of the gas sensor to the detection of the inter-cylinder imbalance to be lowered.

The axial distal end position of the gas introduction part of the sensor element may be more to the axial proximal end side than the axial proximal end position of the inner inlet opening of the inner cover is. In this case, the measurement gas introduced into the inner cover from the inner inlet opening can be caused to reach the gas introduction part of the sensor element quickly through a further shorter distance. Accordingly, the accuracy of detection of the inter-cylinder imbalance of an internal combustion engine and the responsiveness to the detection of the inter-cylinder imbalance can be further increased. When the inner inlet opening is provided plurally, it is preferable that the axial distal end position of the gas introduction part of the sensor element is more to the axial proximal end side than the axial proximal end positions of all the inner inlet openings are.

The axial distal end position of the sensor element may be more to the axial distal end side than the axial proximal end position of the inner inlet opening of the inner cover is. In this case, the measurement gas introduced into the inner cover from the inner inlet opening can be caused to reach the gas introduction part of the sensor element quickly through a further shorter distance. Accordingly, the accuracy of detection of the inter-cylinder imbalance of an internal combustion engine and the responsiveness to the detection of the inter-cylinder imbalance can be further increased. When the inner inlet opening is provided plurally, it is preferable that the axial distal end position of the gas introduction part of the sensor element is more to the axial distal end side than the axial proximal end positions of all the inner inlet openings are.

The inner cover may be provided with a louver part inside the inner inlet opening for blocking the flow of the measurement gas and causing the measurement gas to flow toward the axial proximal end side. In this case, most part of the measurement gas can be caused to flow toward the axial proximal end side within the inner cover from the inner inlet opening through the louver part. As a result, the distance which the measurement gas introduced into the inner cover from the inner inlet opening can be reduced more appropriately.

The louver part may be bent inward of the inner cover from the end portion on the axial distal end side of the inner inlet opening, and formed so as to extend toward the axial proximal end side. In this case, the louver part can be formed easily by cutting it open from the inner cover. Incidentally, the states in which the louver part is formed so as to extend toward the axial proximal end side includes a state in which the louver part extends in parallel to the axial direction from the end portion on the axial distal end side of the inner inlet opening toward the axial proximal end side, and a state in which the louver part extends inclined to the axial direction from the end portion on the axial distal end side of the inner inlet opening toward the axial proximal end side.

The louver opening degree or the shortest distance between a portion of the inner cover which is more to the axial proximal end side than the inner inlet opening of the inner cover is and louver part may be smaller than or equal to 2.0 mm. In this case, the flow rate of the measurement gas introduced into the inner cover from the inner inlet opening through the louver part can be controlled appropriately, and the responsiveness of the gas sensor to the detection of the inter-cylinder imbalance can be further increased. When the louver opening degree exceeds 2.0 mm, there is a concern that the flow rate of the measurement gas introduced into the inner cover from the inner inlet opening through the louver part may not be controlled appropriately.

The axial distal end position of the outer inlet opening of the outer cover may be more to the axial proximal end side than the axial proximal end position of the inner inlet opening of the inner cover is. In this case, the measurement gas introduced into the outer cover from the outer inlet opening (between the outer cove and the inner cover) flows toward the axial distal end side, changes its direction on its way, and flows into the inner cover from the inner inlet opening. At this time, since the masses of water drops flowing together with the measurement gas are larger than that of the measurement gas, the water drops flows directly to the axial distal end side due to their own weights. Accordingly, since the measurement gas and water drops can be separated easily, the effect of preventing water drops from entering the inner cover can be further increased. As a result, flooding of the sensor element and resultant cracking of the sensor element can be further prevented. In addition, it is possible to sufficiently ensure the accuracy of detection of the inter-cylinder imbalance of an internal combustion engine and the responsiveness to the detection of the inter-cylinder imbalance while increasing the resistance to flooding. Incidentally, the axial distal end position of the outer inlet opening of the outer cover may be more to the axial distal end side than the axial proximal end position of the inner inlet opening of the inner cover.

First Embodiment

Figure 2:
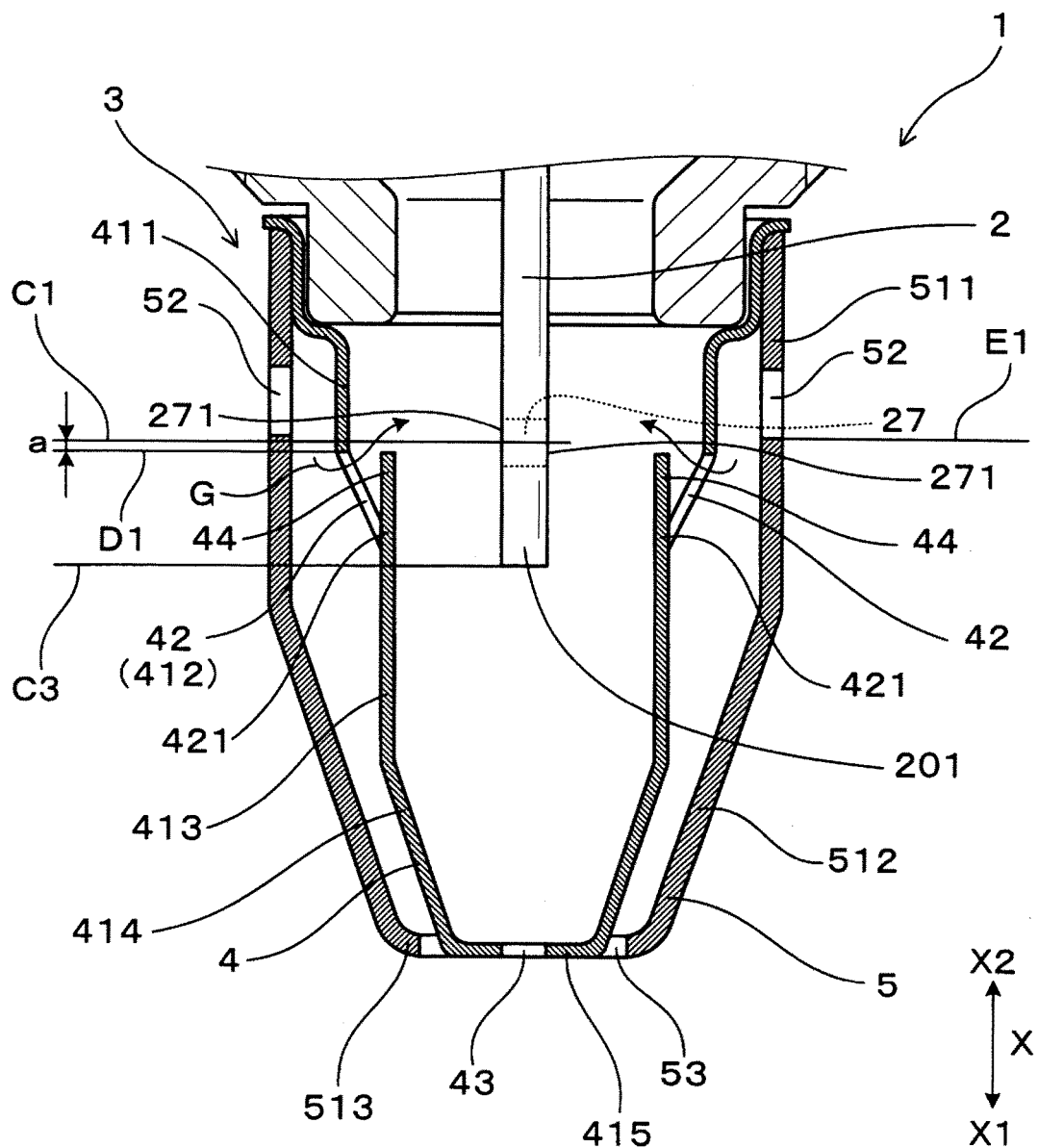
FIG. 2 is a cross-sectional explanatory view showing a structure of an element cover of the gas sensor according to the first embodiment.

An embodiment of the gas sensor is explained with reference the drawings. As shown in FIGS. 1 and 2, the gas sensor 1 of this embodiment includes a sensor element 2 for detecting a concentration of a specific gas in a measurement gas G, a housing 13 holding the sensor element 2 inserted thereinto, and an element cover 3 disposed on the axial distal end side X1 of the housing 13. The sensor element 2 is provided with a gas introduction part 271 at a distal end portion 201 thereof for introducing the measurement gas G thereinto.

As shown in this drawing, the element cover 3 includes an inner cover 4 disposed so as to cover the distal end portion 201 of the sensor element 2 and an outer cover 5 disposed outside the inner cover 4. The outer cover 5 is provided with outer inlet openings 52 for introducing the measurement gas G into the outer cover 5. The inner cover 4 is provided with inner inlet openings 42 for introducing the measurement gas G into the inner cover 4. The axial intermediate position C1 of the gas introduction part 271 of the sensor element 2 is more to the axial proximal end side X2 than the axial proximal end positions D1 of the inner inlet openings 42 of the inner cover 4 are. In the following, the gas sensor 1 of this embodiment is explained in further detail.

As shown in FIG. 1, in this embodiment, the words "axial distal end side X1" means one side of the axial direction X of the gas sensor 1, or the side at which the gas sensor 1 is exposed to the measurement gas G. The words "axial proximal end side X2" means the side opposite to it. As shown in this drawing, in the gas sensor 1, the plate-like sensor element 2 is inserted and held inside a first insulator 11. The first insulator 11 is held inside the housing 13.

Figure 4:
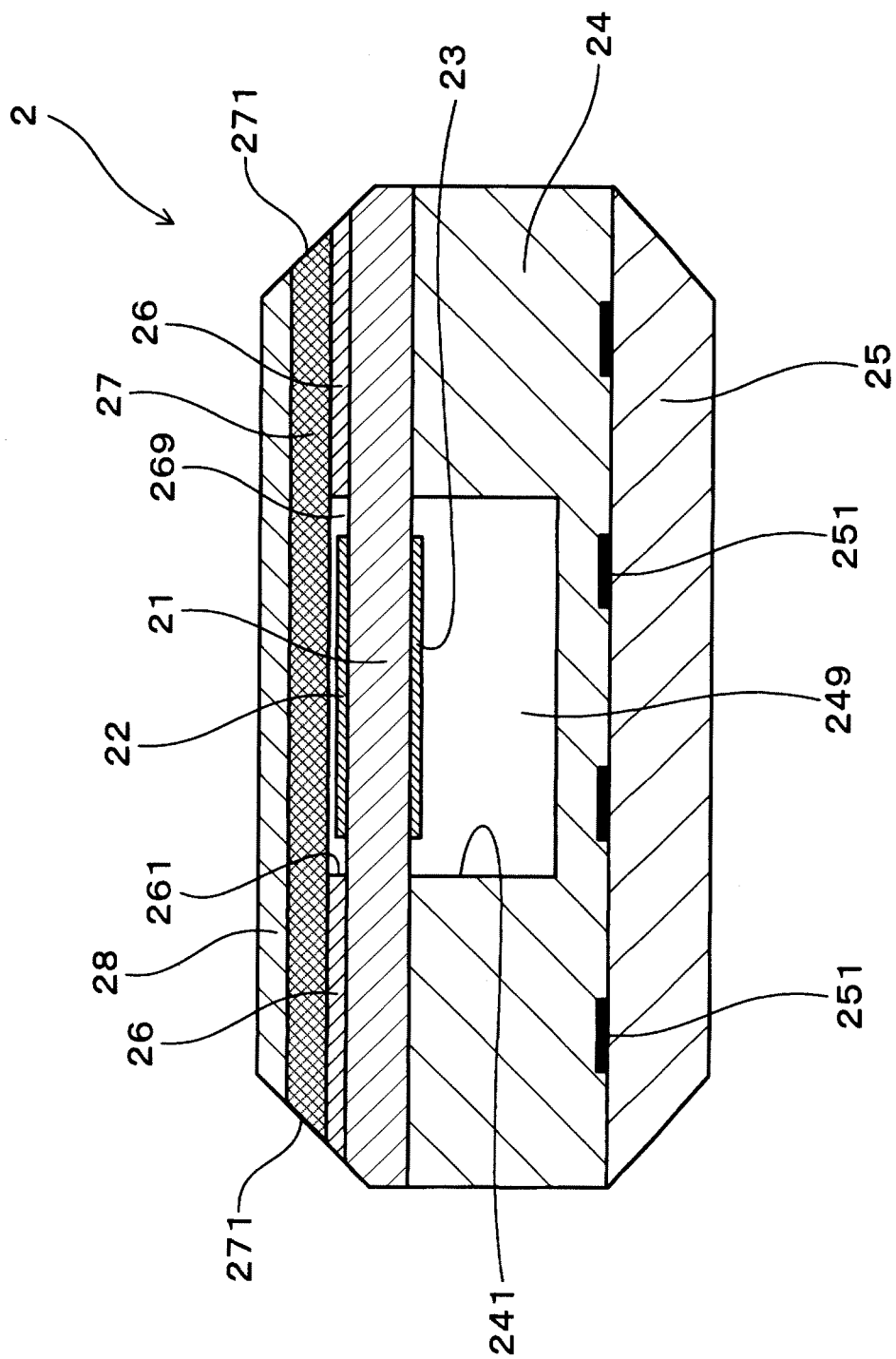
FIG. 4 is a cross-sectional explanatory view showing a structure of a distal end portion of the sensor element of the first embodiment.

As shown in FIG. 4, the sensor element 2 is an A/F sensor element which detects an air/fuel ration (A/F) of a fuel air mixture supplied to an internal combustion engine based on a limit current flowing between electrodes (a later-described measurement gas-side electrode 22 and a reference gas-side electrode 23) depending on the specific gas concentration (oxygen concentration) in the measurement gas G (exhaust gas). Incidentally, FIG. 4 is a drawing showing the cross section perpendicular to the axial direction X in the distal end portion 201 of the sensor element 2.

As shown in this drawing, the sensor element 2 includes an oxygen ion-conductive solid electrolyte body 21 made of zirconia. The measurement gas-side electrode 22 which should be contacted with the measurement gas G is provided on one surface of the plate-like solid electrolyte body 21, and provided with the reference gas-side electrode 23 which should be contacted with the reference gas (atmosphere) on the other surface.

As shown in this drawing, a reference gas chamber-forming layer 24 made of alumina is stacked on the solid electrolyte body 21 at the side of the reference gas-side electrode 23. The reference gas chamber-forming layer 24 is provided with a groove portion 241 to form a reference gas chamber 249. The reference gas chamber 249 is configured so as to be capable of introducing the reference gas therein.

A heater board 25 is stacked on the surface of the reference gas chamber-forming layer 24 at the side opposite to the solid electrolyte body 21. The heater board 25 is provided with a heating body (heater) 251 which generates heat by energization so as to be opposed to the reference gas chamber-forming layer 24. The heat generating body 251 is configured to heat the sensor element 2 to an activation temperature by being caused to generate heat by energization.

As shown in this drawing, an insulating layer 26 made of alumina is stacked on the solid electrolyte body 21 at the side of the measurement gas-side electrode 22. The insulating layer 26 includes an opening 261. A porous diffusion resistance layer 27 made of alumina porous material allowing the measurement gas G to transmit therethrough is stacked on the surface opposite to the solid electrolyte body 21 of the insulating layer 26. Part of the diffusion resistance layer 27 is exposed to the outer surface of the sensor element 2. The gas introduction part 271 is formed in the exposed part at a plurality of positions.

A measurement gas chamber 269 is formed in a place surrounded by the solid electrolyte body 21, the insulating layer 26 and the diffusion resistance layer 27. The measurement gas chamber 269 is configured to allow the measurement gas G transmitted through the diffusion resistance layer 27 to be introduced therein. A shielding layer 28 made of alumina is stacked on the surface of the diffusion resistance layer 27 at the side opposite to the insulating layer 26. Although omitted from illustration, a protecting layer or the like for trapping poisoning components in the measurement gas G may be formed on the outer surface of the sensor element 2 so as to cover the exposed portion (gas introduction part 271) of the diffusion resistance layer 27 of the sensor element 2.

As shown in FIG. 1, a first proximal end-side cover 14 is fixed to the axial proximal end side X2 of the housing 13 so as to cover a proximal end portion 202 of the sensor element 2, and a second proximal end-side cover 15 is fixed to the axial proximal end side X2 of the first proximal end-side cover 14. The second proximal end-side cover 15 is provided with ventilation holes 151 for introducing the atmosphere. The proximal end side opening of the second proximal end-side cover 15 is closed by a sealing member 16 made of a rubber bush. Lead members 17 to be connected to the outside are provided penetrating through the sealing member 16.

A second insulator 12 covering the proximal lend portion 202 of the sensor element 2 is disposed on the axial proximal end side X2 of the first insulator 11 within the first proximal end-side cover 14. Metal terminals 18 connected to the lead members 17a are disposed in the second insulator 12. The metal terminals 18 are in contact with the electrode terminals of the sensor element 2 for providing electric conduction.

As shown in this figure, the element cover 3 for protecting the sensor element 2 is disposed on the distal end side of the housing. The element cover 3 includes the bottomed and cylindrical inner cover 4 disposed so as to cover the distal end portion 201 of the sensor element 2 and the bottomed and cylindrical outer cover 5 disposed outside the inner cover 4. The inner cover 4 is fixed to the distal end portion of the housing 13. The outer cover 5 is fixed to the proximal end portion of the inner cover 4.

As shown in FIG. 2, the outer cover 5 includes, in the order from the axial proximal end side X2, an outer side surface portion 511 whose diameter is roughly constant in the axial direction X, an outer reduced-diameter portion 512 having a tapered shape whose diameter is reduced toward the axial distal end side X1 and an outer bottom surface portion 513 closing the axial distal end side X1. The outer inlet openings 52 are provided in the outer side surface portion 511 at a predetermined interval along the circumferential direction. The axial distal end position E1 of the outer inlet openings 52 is more to the axial proximal end side X2 than the axial proximal end position D1 of the inner inlet openings 42 of the inner cover 4 is. The outer bottom surface portion 513 is provided with an outer discharge opening 53.

As shown in in this figure, the inner cover 4 includes, in the order from the axial proximal end side X2, a first inner side surface portion 411 whose diameter is roughly constant in the axial direction X, a first inner diameter-reduced portion 412 having a tapered shape whose diameter is reduced toward the axial distal end side X1, a second inner side surface portion 413 whose diameter is roughly constant in the axial direction X, a second inner diameter-reduced portion 414 having a tapered shape whose diameter is reduced toward the axial distal end side X1, and an inner bottom surface portion 415 closing the axial distal end side X1. The inner bottom surface portion 415 is disposed on roughly the same plane as the outer bottom surface portion 513 of the outer cover 5 within the outer discharge opening 53.

The first inner diameter-reduced portion 412 are provided with the inner inlet openings 42 at a predetermined interval along the circumferential direction. The inner inlet openings 42 are disposed concentrically to the center axis of the gas sensor 1 on a plane perpendicular to the axial direction X. That is, all of the inner inlet openings 42 are the same in their axial positions. The axial proximal end positions D1 of all the inner inlet openings 42 are more to the axial distal end side X1 than the axial distal end position E1 of the outer inlet openings 52 of the outer cover 5 are. All of the inner inlet openings 42 are formed in a louver shape. That is, the first inner diameter-reduced portion 412 are provided with a louver part 44 which blocks a flow of the measurement gas G in the respective inner positions at which the inner inlet openings 42 are provided, to cause the measurement gas G to flow toward the axial proximal end side X2. The inner bottom surface portion 415 is provided with an inner discharge opening 43.

As shown in this drawing, the axial intermediate position C1 of the gas introduction part 271 of the sensor element 2 is more to the axial proximal end side X2 than the axial proximal end position D1 of the inner inlet opening 42 of the inner cover 4 is. In this embodiment, it is more to the axial proximal end side X2 than the axial proximal end positions D1 of all of the inner inlet openings 42 are. The axial distal end position C3 of the sensor element 2 is more to the axial distal end side X1 than the inner inlet opening 42 of the inner cover 4 is. In this embodiment, it is more to the axial distal end side X1 than the axial proximal end positions D1 of all of the inner inlet opening 42 are.

The distance from the axial proximal end position D1 of the inner inlet opening 42 of the inner cover 4 to the axial intermediate position C1 of the gas introduction part 271 of the sensor element 2 a is 0 mm<a≤3.0 mm. Preferably, the axial direction a is 0 mm<a≤3.0 mm, and more preferably, 0.7 mm≤a≤3.0 mm.

Figure 3:
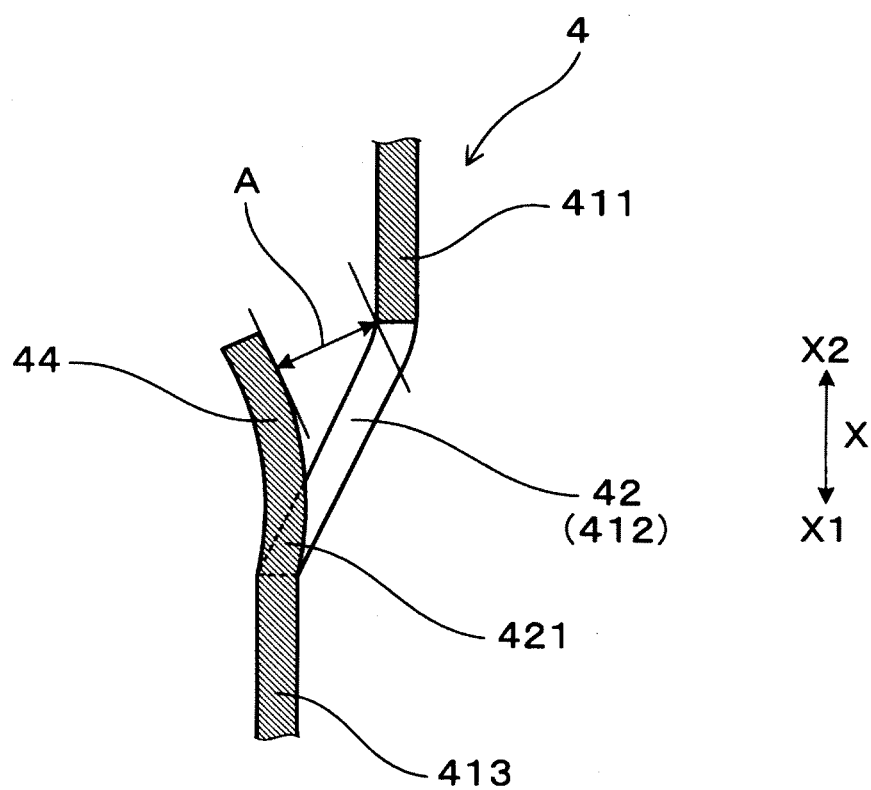
FIG. 3 is a cross-sectional explanatory view showing an inner inlet opening and louver part of an inner cover of the first embodiment.

As shown in FIG. 3, the louver part 44 is bent inward from an end portion 421 on the axial distal end side X1 of the inner inlet opening 42 to the inner cover 4, and formed so as to extend toward the axial proximal end side X2. The louver part 44 is formed in a roughly square shape. The louver part 44 is formed by extruding part of the inner cover 44 with a mold or the like. The louver opening degree A or the shortest distance between a portion (the first inner side surface portion 411 of this embodiment) of the inner cover 4 which is more to the axial proximal end side X2 than the inner inlet opening 42 is set smaller than or equal to 2.0 mm.

Figure 5:
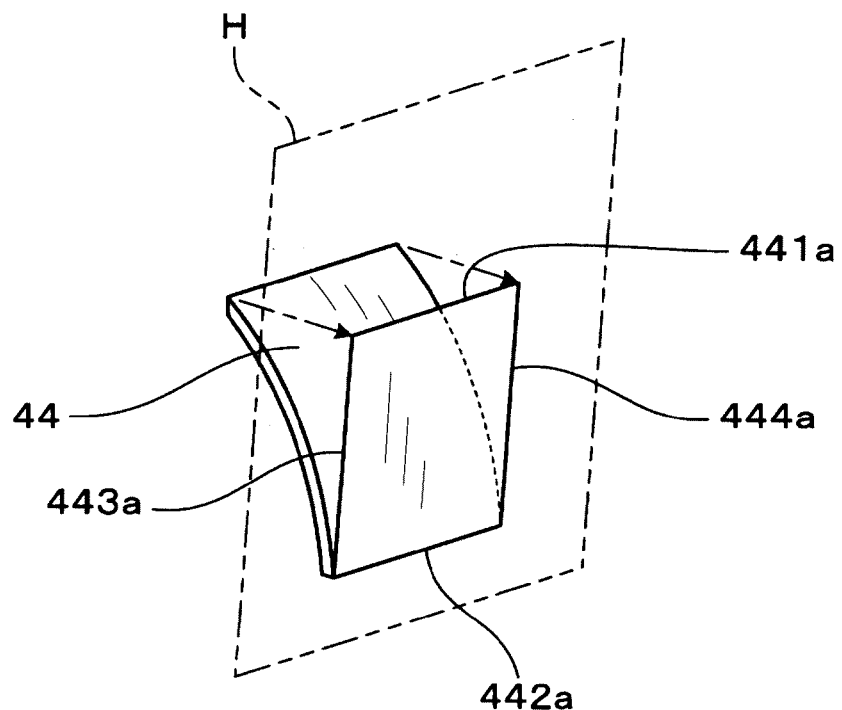
FIG. 5 is an explanatory view showing a louver part in a state of being projected onto the same plane as the inner inlet opening in the first embodiment.
Figure 6:
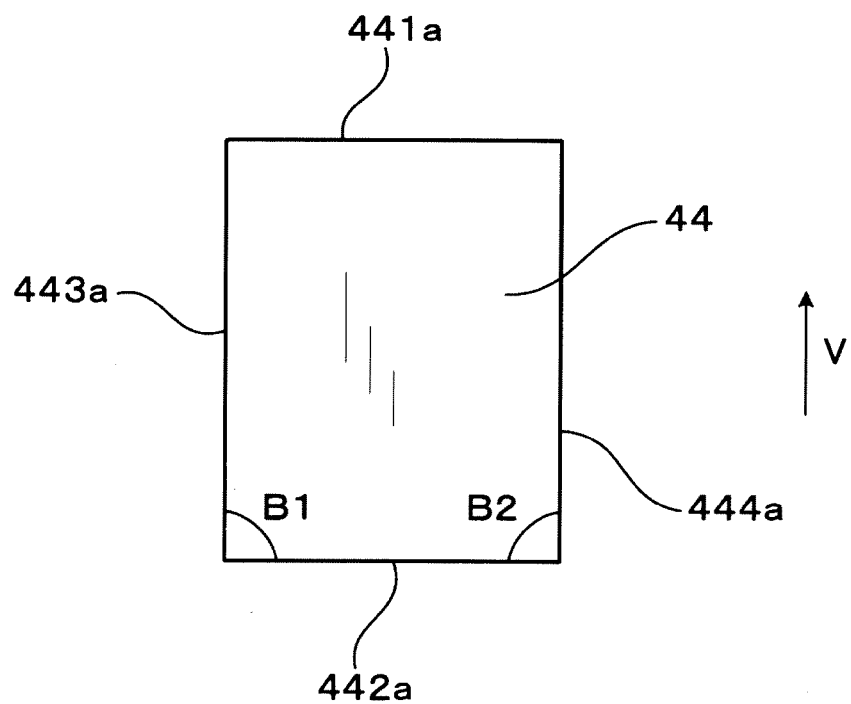
FIG. 6 is an explanatory view showing the louver part projected onto the same plane as the inner inlet opening in the first embodiment.

As shown in FIGS. 5 and 6, when the louver part 44 is projected onto the same plane (plane H) as the inner inlet opening 42, the louver part 44 includes a distal end side edge 441a, a base side edge 442a and a pair of side end edges 443a and 444a. The pair of the side end edges 443a and 444a are formed roughly linearly and in roughly parallel to the louver forming direction V extending from the base side to the distal end side of the louver part 44. The angles B1 and B2 between the base side edge 442a and the pair of the side end edges 443a and 444a of the louver part 44 are 90 degrees. FIGS. 5 and 6 show the louver part 44 as taken out from the inner cover 4.

As shown in FIG. 2, the end portion on the axial proximal end side X2 of the louver part 44 is at approximately the same position in the axial direction X as the end portion on the axial proximal end side X2 of the inner inlet opening 42. The measurement gas G which is going to flow from the space between the outer cover 5 and the inner cover 4 into the inner cover 4 through the inner inlet opening 42 is blocked by the louver part 44, and accordingly does not flow toward the axial distal end side X1. Although part of this measurement gas G is going to flow from the pair of the side end edges 443a and 444a into the inner cover 4, most of the measurement gas G flows to the axial proximal end side X2 along the louver part 44.

Next, advantageous effects of the gas sensor 1 of this embodiment are explained. In the gas sensor 1 of this embodiment, the sensor element 2 is provided with the gas introduction part 271 for introducing the measurement gas G thereinto at the distal end portion 201 thereof. The inner cover 4 covering the distal end portion 201 of the sensor element 2 is provided with the inner inlet openings 42 for introducing the measurement gas G into the inner cover 4. The axial intermediate position C1 of the gas introduction part 271 of the sensor element 2 is more to the axial proximal end side X2 than the axial proximal end position D1 of the inner inlet openings 42 of the inner cover 4 is. The louver part 44 is provided at the inner position of the inner inlet openings 42 in the inner cover 4 so that the measurement gas G flowing from the inner inlet openings 42 into the inner cover 4 flows to the axial proximal end side X2.

Figure 7:
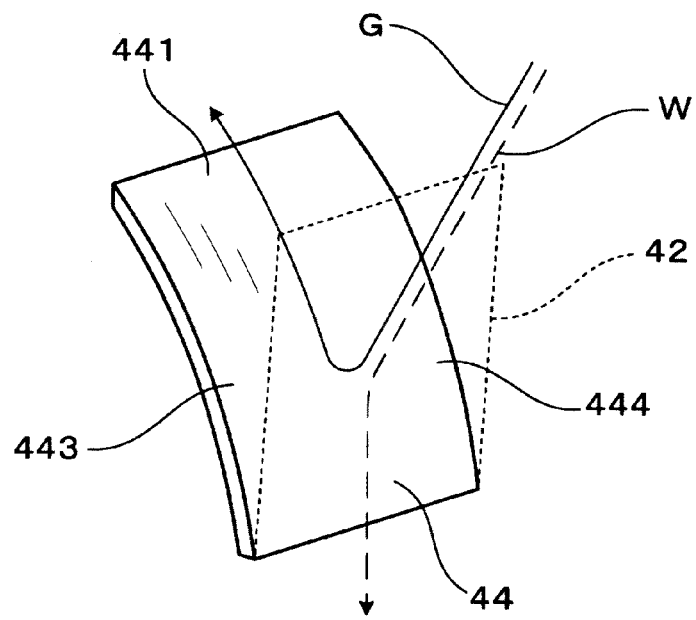
FIG. 7 is an explanatory view showing a flow of a measurement gas flowing into the inner cover from the inner inlet opening through the louver part in the first embodiment.

As a result, as shown in FIG. 7, most of the measurement gas G which is going to flow from the inner inlet opening 42 into the inner cover 4 can be caused to flow to the axial proximal end side X2 by the louver part 44. Since the axial intermediate position C1 of the gas introduction part 271 is more to the axial proximal end side X2 than the axial proximal end position D of the inner inlet openings 42, the measurement gas G introduced into the inner cover 4 from the inner inlet openings 42 can be caused to reach the gas introduction part 271 of the sensor element 2 quickly through a distance as short as possible. Further, the measurement gas G can be caused to reach the gas introduction part 271 of the sensor element 2 without mixing with the measurement gas G having flowed in from another inner inlet opening 42. Further, the measurement gases G of the respective cylinders of an internal combustion engine can be caused to reach the gas introduction part 271 of the sensor element 2 in succession, so that the measurement gases G from the respective cylinders do not mix with one another before reaching the gas introduction part 271 of the sensor element 2.

As a result, since the responsiveness of the gas sensor 1 can be increased, change of the output (air/fuel ratio: A/F) of the gas sensor 1 as an index of the inter-cylinder imbalance of the internal combustion engine can be detected with more precision. Thus, the accuracy of detection to the inter-cylinder imbalance of an internal combustion engine of the gas sensor 1 can be increased.

Figure 8:
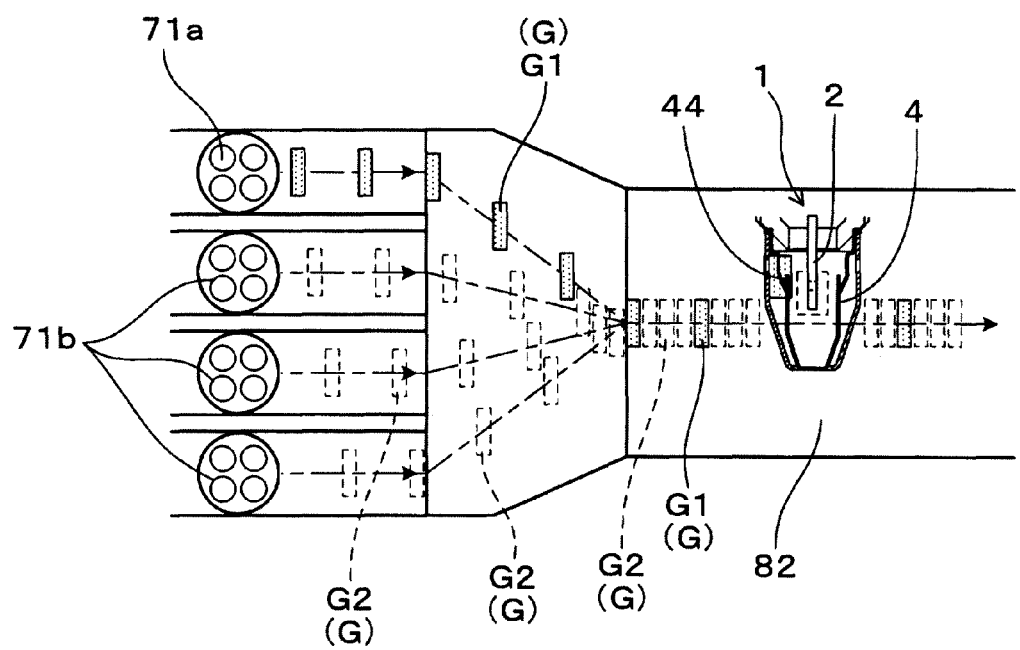
FIG. 8 is an explanatory view showing a flow of a measurement gas in a multi-cylinder internal combustion engine in the first embodiment.
Figure 9:
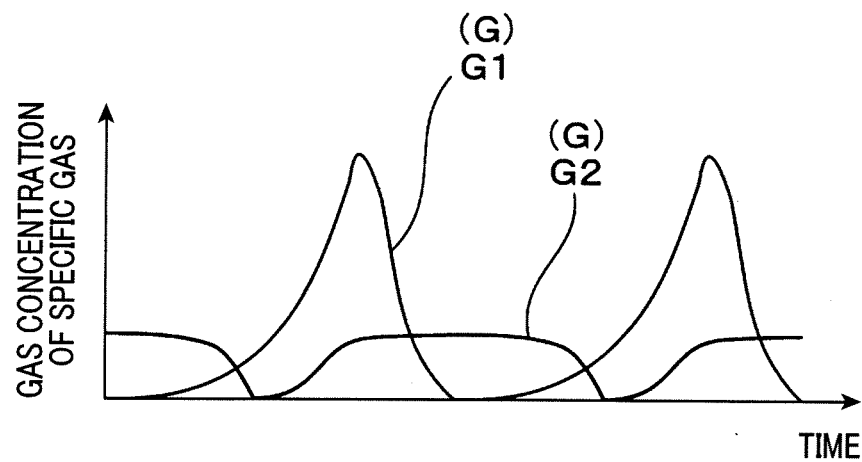
FIG. 9 is a graph showing temporal change of a gas concentration of a specific gas with the horizontal axis representing time and the vertical axis representing the gas concentration.

In FIG. 8, there is shown a flow of the measurement gas G (exhaust gas) in an exhaust pipe 82 when the air/fuel ratio of one cylinder 71a is on the rich side, and the air/fuel ratio of another cylinder 71b is on the lean side in a multi-cylinder internal combustion engine. As shown in this figure, exhausts from the cylinders 71a and 71b are performed in succession, and the measurement gas G1 on the rich side and the measurement gas G2 on the lean side reach the gas sensor 1 within the exhaust pipe 82 in succession. FIG. 9 shows temporal variations of gas concentration of the measurement gases G measured by the gas sensor 1. As shown in this drawing, in the gas sensor 1, the measurement gas G1 on the rich side, and the measurement gas G2 on the lean side G2 are measured alternately.

Since the measurement gases G flowing into the inner cover 4 successively in time are in a state of being difficult to mix with each other, the measurement gas G1 on the rich side and the measurement gas G2 on the lean side which are reaching at a predetermined time interval can be made difficult to mix with each other. In this embodiment, the distance through which the measurement gas G flowing to the axial proximal end side X2 along the louver part 44 reaches the gas introduction part 271 of the sensor element 2 is made short. Accordingly, the accuracy of detection of the inter-cylinder imbalance in the gas sensor 1 can be increased by suppressing the measurement gases G discharged successively in time from mixing with each other.

In this embodiment, the axial distal end position C3 of the sensor element 2 is more to the axial distal end side X1 than the axial proximal end position D1 of the inner inlet openings 42 of the inner cover 4 is. Therefore, the measurement gas G introduced into the inner cover 4 from the inner inlet openings 42 can be caused to reach the gas introduction part 271 of the sensor element 2 quickly through a further shorter distance. Accordingly, the accuracy of detection of the inter-cylinder imbalance of an internal-combustion engine and the responsiveness to the detection of the inter-cylinder imbalance can be further increased.

When the louver part 44 is projected onto the same plane (plane H) as the inner inlet opening 42, the pair of the side end edges 443*a* and 444*a* are formed roughly linearly and in roughly parallel to the louver forming direction V extending from the base side to the distal end side of the louver part 44. Accordingly, as shown in FIG. 7, the measurement gas G flows easily from the base side to the distal end side of the louver part 44 along the surface of the louver part 44. It is possible to suppress part of the measurement gas G from leaking to both sides from side end portions 443 and 444 of the louver part 44 and flowing into the inner cover 4. That is, it is possible to further increase the percentage of the flow of the measurement gas G flowing in through the distal end portion 441 of the louver part 44.

The louver opening degree A or the shortest distance between the portion (the first inner side surface portion 411) more to the axial proximal end side X2 than the inner inlet opening 42 is and the louver part 44 in the inner cover 4 is set smaller than or equal to 2.0 mm. Accordingly, it is possible to control the flow rate of the measurement gas G introduced into the inner cover 4 from the inner inlet opening 42 through the louver part can be controlled appropriately, and the responsiveness of the gas sensor 1 can be further increased.

The axial distal end position E1 of the outer inlet opening 52 of the outer cover 5 is more to the axial proximal end side X2 than the axial proximal end position D1 of the inner inlet opening 42 of the inner cover 4. Accordingly, as shown in FIG. 7, the measurement gas G introduced into the outer cover 5 (between the outer cove 5 and the inner cover 4) flows toward the axial distal end side X1, changes its direction on its way, and flows into the inner cover 4 from the inner inlet opening 42. At this time, since the masses of water drops W flowing together with the measurement gas G are larger than that of the measurement gas G, they flow directly to the axial distal end side X1 due to their own weights.

Accordingly, since the measurement gas G and the water drops W can be separated easily, the effect of preventing the water drops W from entering the inner cover 4 can be further increased. As a result, flooding of the sensor element 2 and resultant cracking of the sensor element 2 can be prevented. In addition, it is possible to sufficiently ensure the responsiveness of the gas sensor 1 and the accuracy of detection of the inter-cylinder imbalance of an internal combustion engine while increasing the resistance to flooding. Incidentally, the water drops W having been separated are discharged to the outside from the outer discharge opening 53 of the outer cover 5.

As described above, according to this embodiment, it is possible to provide the gas sensor 1 which is excellent in the accuracy of detection of the inter-cylinder imbalance of an internal combustion engine and in the responsiveness to the detection of the inter-cylinder imbalance.

Figure 10:
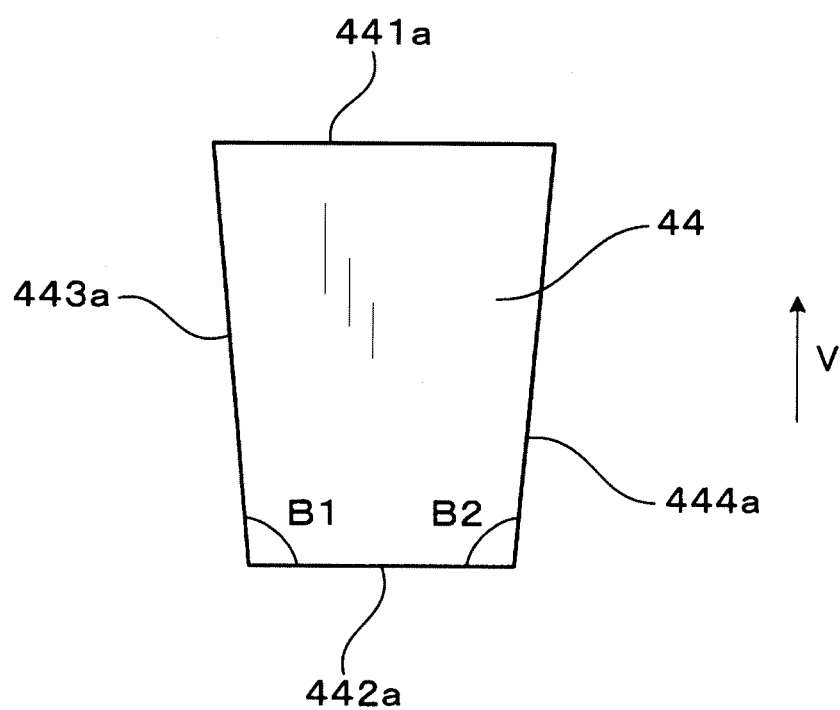
FIG. 10 is an explanatory view showing a modification of the louver part projected onto the same plane as the inner inlet opening.

In this embodiment, as shown in FIGS. 5 and 6, when the louver part 44 is projected onto the same plane (plane H) as the inner inlet opening 42, the pair of the side end edges 443*a* and 444*a* are formed roughly linearly and in roughly parallel to the louver forming direction V. Other than that, as shown in FIG. 10, the pair of the side end edges 443*a* and 444*a* of the louver part 44 may be formed roughly linearly and inclined outward to the louver forming direction V. That is, the angles B1 and B2 between the base side edge 442*a* and the pair of the side end edges 443*a* and 444*a* of the louver part 44 may exceed 90 degrees (larger than 90 degrees and smaller than 95 degrees, for example).

Figure 11:
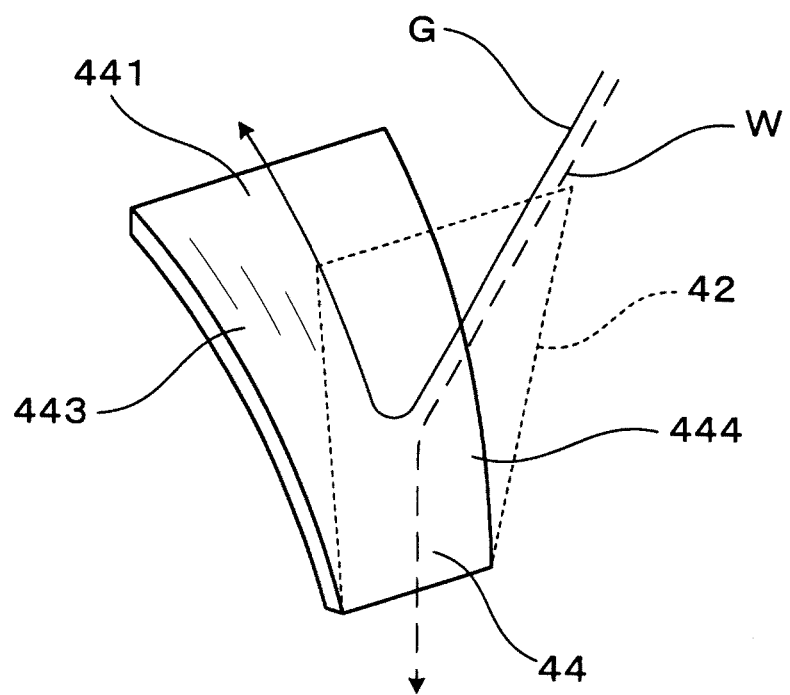
FIG. 11 is an explanatory view showing a flow of the measurement gas flowing into the inner cover from the inner inlet opening through the modification of the louver part in the first embodiment.

In the case of the above configuration, as shown in FIG. 11, the measurement gas G flows more easily from the base side to the distal end side of the louver part 44 along the surface of the louver part 44. It is possible to suppress part of the measurement gas G from leaking to both sides from the side end portions 443 and 444 of the louver part 44 and flowing into the inner cover 4. That is, it is possible to further increase the percentage of the flow of the measurement gas G flowing in through the distal end portion 441 of the louver part 44. As a result, the accuracy of detection of the inter-cylinder imbalance of an internal-combustion engine and the responsiveness to the detection of the inter-cylinder imbalance can be further increased.

Second Embodiment

Figure 12:
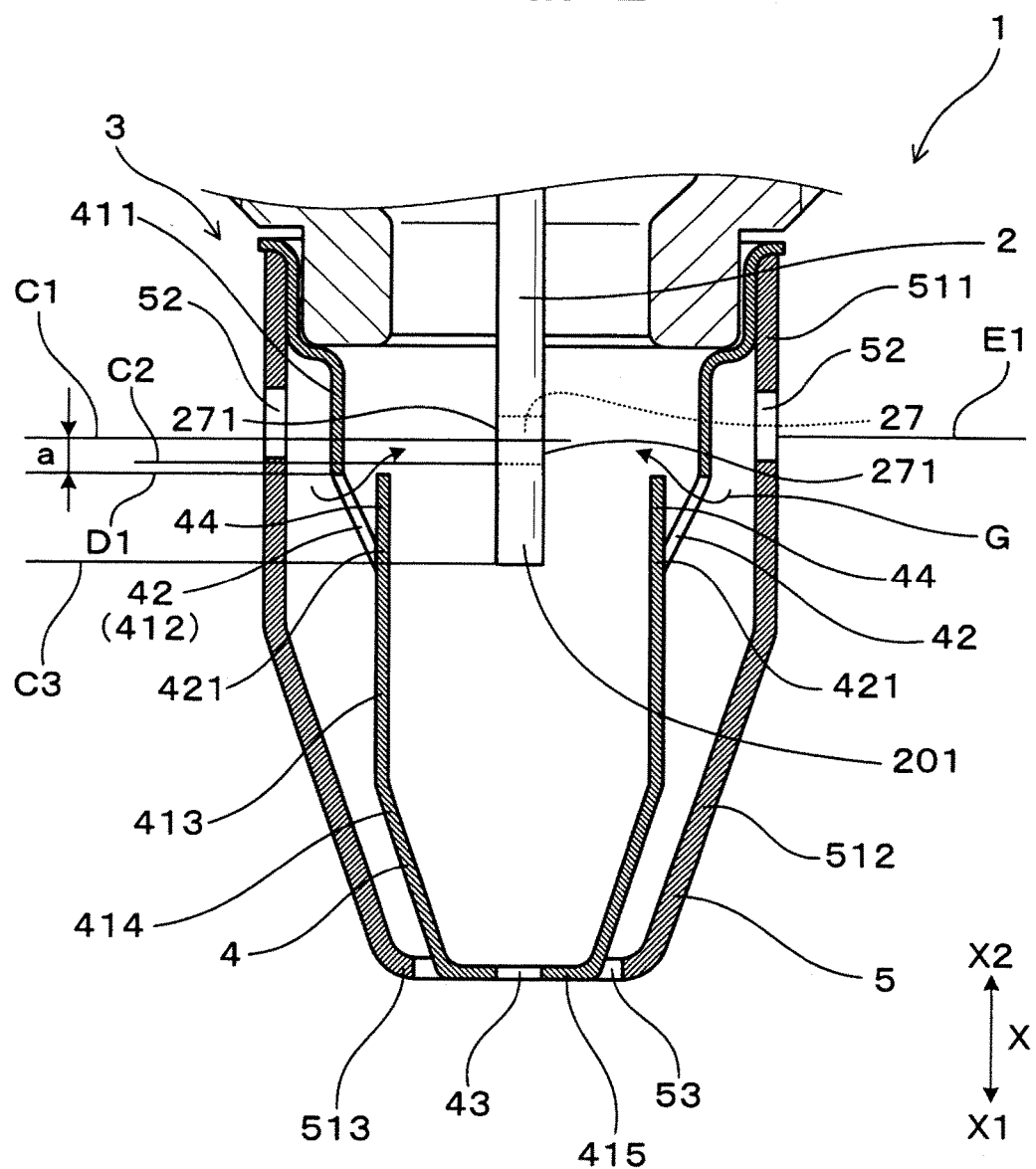
FIG. 12 is a cross-sectional explanatory view showing a structure of an element cover of a gas sensor according to a second embodiment of the invention.
Figure 13:
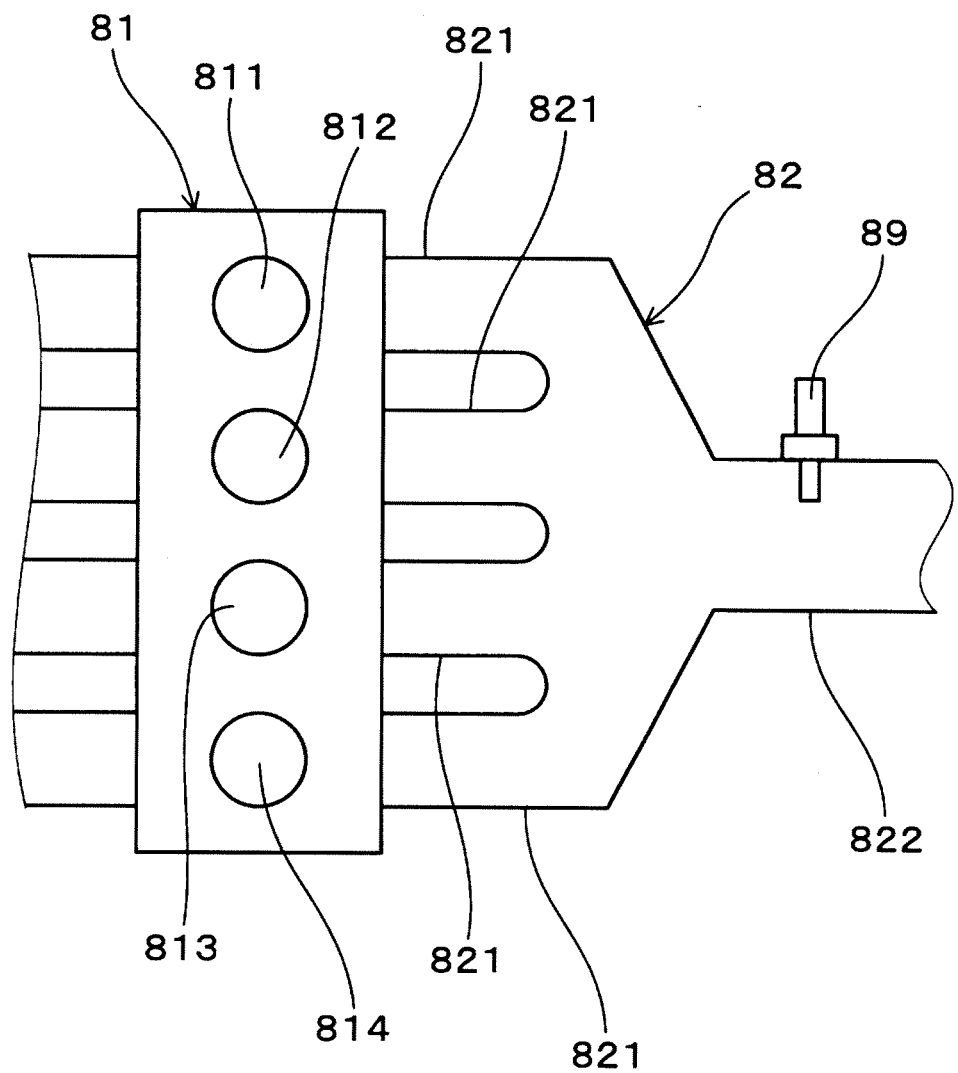
FIG. 13 is an explanatory view showing an exhaust pipe of an internal combustion engine on which a gas sensor according to a third embodiment of the invention is mounted.

As shown in FIG. 12, this embodiment is an example in which the positional relationship between the gas introduction part 271 of the sensor element 2 and the inner inlet openings 42 of the inner cover 4 is changed. As shown in this figure, the axial distal end position C2 of the gas introduction part 271 of the sensor element 2 is more to the axial proximal end side X2 than the axial proximal end position D1 of the inner inlet opening 42 of the inner cover 4 is. In this embodiment, the axial distal end position C2 of the gas introduction part 271 is more to the axial proximal end side X2 than the axial proximal end positions D1 of all the inner inlet opening 42. The other basic structures are the same as the first embodiment. The structures which are the same as those of the first embodiment are followed by the same reference signs and explanation thereof are omitted.

The louver part 44 is provided at the inner position of the inner inlet opening 42 of the inner cover 4 of this embodiment to cause the measurement gas G flowing into the inner cover 4 from the inner inlet opening 42 to flow to the axial proximal end side X2 like the first embodiment. Most of the measurement gas G flowing into the inner cover 4 from the inner inlet opening 42 flows to the axial proximal end side X2. Accordingly, the measurement gas G introduced into the inner cover 4 from the inner inlet opening 42 through the louver part 44 can be caused to reach the gas introduction part 271 of the sensor element 2 quickly through a further shorter distance by making the axial distal end position C2 of the gas introduction part 271 more to the axial proximal end side X2 than the axial proximal end position D1 of the inner inlet opening 42 is. As a result, the accuracy of detection of the inter-cylinder imbalance of an internal-combustion engine and the responsiveness to the detection of the inter-cylinder imbalance can be further increased. The other basic advantageous effects are the same as the first embodiment.

Third Embodiment

This embodiment evaluates the accuracy of detection of the inter-cylinder imbalance of an internal combustion engine for the gas sensors. For this embodiment, there were prepared a plurality of the gas sensors which are different from one another in the axial distance a from the axial proximal end positions of the inner inlet openings of the inner cover to the axial intermediate position of the gas introduction part of the sensor element (see FIG. 2). The other basic structures of the prepared gas sensors are the same as the gas sensor of the first embodiment (see FIGS. 1 to 4 and so on).

Next, a method for evaluating the accuracy of the detection of the inter-cylinder imbalance of an internal combustion engine is explained. In this embodiment, an in-line four-cylinder internal combustion engine having four cylinders (a first cylinder 811, a second cylinder 812, a third cylinder 813 and a fourth cylinder 814) as shown in FIG. 3. was prepared. The respective cylinders 811 to 814 of the internal combustion engine 81 are in communication with exhaust branch parts 821 of an exhaust pipe 82, respectively. The four exhaust branch parts 821 join on the downstream side to communicate with an exhaust common part 822 of the exhaust pipe 82. A gas sensor 89 was mounted on the exhaust common part 822 of this exhaust pipe 82.

Next, the internal combustion engine was operated under a predetermined condition. In this embodiment, the rotational speed was set to 1600 rpm, and an adjustment was made so that the gas flow rate per unit cross-sectional area within the exhaust pipe becomes 20 g/sec. For the second cylinder of the four cylinders of the internal combustion engine, the fuel injection amount was increased excessively compared to the other cylinders. In this embodiment, an adjustment was made so that the air/fuel ratio of the second cylinder is in a state of being shifted to the rich side by 40% (in a state in which the fuel injection amount is increased by 40%) from the theoretical air fuel ratio.

Figure 14:
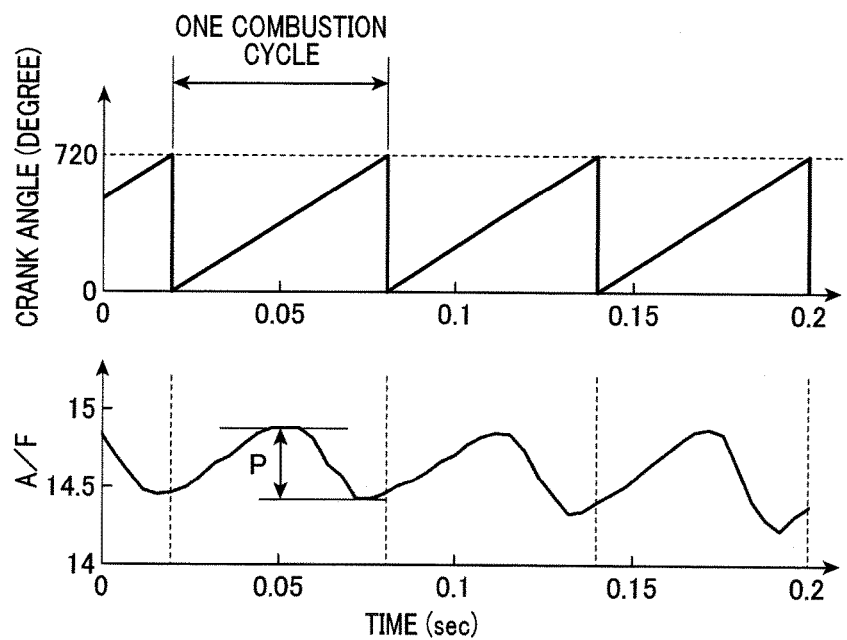
FIG. 14 is a graph showing temporal changes of a crank angle and A/F in the third embodiment.

As shown in FIG. 14, the output value (air/fuel ratio: A/F) of the gas sensor was obtained with time. Here, the waveform of the output value of the gas sensor changes with one combustion cycle of the internal combustion engine being its one cycle. One combustion cycle of the internal combustion engine starts at the moment when the crank angle is 0 degrees and ends at the moment when the crank angle is 720 degrees. During one combustion cycle, the combustion is performed in the order of the first cylinder, the third cylinder, the fourth cylinder and the second cylinder. Since discharge is performed after combustion in each of the cylinders, the discharge is performed in the order of the second cylinder, the first cylinder, the third cylinder and the fourth cylinder during one combustion cycle. Accordingly, ideally, the exhaust gases discharged from the respective cylinders reach the gas introduction part of the sensor element of the gas sensor in the order of the second cylinder, the first cylinder, the third cylinder and the fourth cylinder.

Next, a method for evaluating the accuracy of the detection of the inter-cylinder imbalance of an internal combustion engine is explained. As shown in FIG. 14, the amplitude P (difference between the maximum value and the minimum value) of a waveform during one combustion cycle was obtained from a waveform of the obtained output values (air/fuel ratio: A/F) of the gas sensor as an imbalance response value. In this embodiment, the imbalance response value was obtained for each of the gas sensors which are different in the axial distance a from one another. The imbalance response value of the gas sensor whose axial direction a is −1.5 mm (the gas sensor of a conventional feature) was used as a standard (=100%), and imbalance response value ratios (%) of the other gas sensors were obtained. When the imbalance response value is higher, it shows that the accuracy of the detection of the inter-cylinder imbalance of an internal combustion engine is higher.

Figure 15:
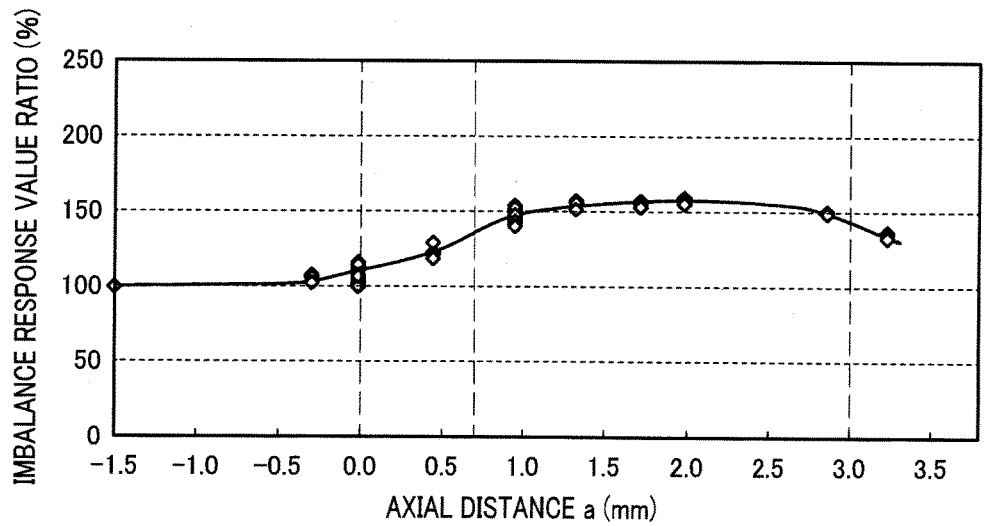
FIG. 15 is a graph showing a relationship between the imbalance response value and the axial distance a between the axial proximal end position of the inner inlet opening and the axial intermediate position of the gas introduction part in the third embodiment.

FIG. 15 shows results of evaluation of the accuracy of the detection of the inter-cylinder imbalance of the internal combustion engine. In this drawing, the horizontal axis represents the axial distance a (mm), and the vertical axis represents the imbalance response value (%). When the axial direction a is 0 mm, it means that the axial intermediate position of the gas introduction part of the sensor element and the axial proximal end position of the inner inlet openings of the inner cover are the same. When the axial direction a is smaller than 0 mm, it means that the axial intermediate position of the gas introduction part of the sensor element is more to the axial distal end side than the axial proximal end position of the inner inlet openings of the inner cover is.

From this drawing, it was found that, when the axial distance a exceeds 0 mm, that is, when the axial intermediate position of the gas introduction part of the sensor element is more to the axial proximal end side than the axial proximal end position of the inner inlet openings of the inner cover is, the imbalance response value increases. Further, it was found that, when the axial distance a exceeds 0.7 mm, the imbalance response value further increases, and the imbalance response value becomes stable. On the other hand, it was found that, when the axial distance a exceeds 3.0 mm, the imbalance response value decreases.

From the above results, it was found that the responsiveness of the gas sensor can be increased and the accuracy of the gas sensor for the detection of the inter-cylinder imbalance of the internal combustion engine can be improved by setting the axial intermediate position of the gas introduction part of the sensor element more to the axial proximal end side than the axial proximal end position of the inner inlet openings of the inner cover is. Also it was found that, to obtain such advantageous effects sufficiently, it is preferable that the axial distance a from the axial intermediate position of the gas introduction part of the sensor element to the axial proximal end position of the inner inlet openings of the inner cover is larger than or equal to 0.7 mm and smaller than or equal to 3.0 mm.

EXPLANATION OF SYMBOLS

1: gas sensor
13: housing
2: sensor element
201: distal end portion (distal end portion of sensor element)
271: gas introduction part
3: element cover 4: inner cover
42: inner inlet opening
5: outer cover
52: outer inlet opening
C1: axial intermediate position (axial intermediate position of gas introduction part)
D1: axial proximal end position (axial proximal end position of inner inlet opening)
X1: axial distal end side
X2: axial proximal end side

The invention claimed is:

1. A gas sensor comprising:
a sensor element for detecting a concentration of a specific gas contained in a measurement gas, the sensor element being a stacked sensor element formed by stacking an oxygen ion-conductive solid electrolyte body provided with a measurement gas-side electrode and a reference gas-side electrode, and a diffusion resistance layer which allows the measurement gas to transmit therethrough to contact with the measurement gas-side electrode;
a housing holding the sensor element inserted therein; and
an element cover disposed at an axial distal end side of the housing, wherein
the sensor element is provided with a gas introducing part for introducing the measurement gas thereinto at a distal end portion thereof, the gas introduction part being part of the diffusion resistance layer exposed to an outer surface of the sensor element,
the element cover includes an inner cover disposed so as to cover the distal end portion of the sensor element and an outer cover disposed outside the inner cover,
the outer cover is provided with an outer inlet opening for introducing the measurement gas into the outer cover,
the inner cover is provided with an inner inlet opening for introducing the measurement gas into the inner cover,
an axial intermediate position of the gas introduction part of the sensor element is more to an axial proximal end side than an axial proximal end position of the inner inlet opening of the inner cover is,
an axial distal end portion of the sensor element is more to the axial distal end side than the axial proximal end position of the inner inlet opening of the inner cover is, and
an axial distance between the axial intermediate position of the gas introduction part of the sensor element and the axial proximal end position of the inner inlet opening of the inner cover is 0 mm<a≤3.0 mm.

2. The gas sensor according to claim 1, wherein the inner cover is provided with a louver part for blocking a flow of the measurement gas to cause the measurement gas to flow to the axial proximal end side within the inner inlet opening.

3. The gas sensor according to claim 2, wherein the louver part is bent from an end portion on the axial distal end side of the inner inlet opening to inside of the inner cover, and formed so as to extend toward the axial proximal end side.

4. The gas sensor according to claim 1, wherein an axial distal end position of the outer inlet opening of the outer cover is more to the axial proximal end side than the axial proximal end position of the inner inlet opening of the inner cover is.

5. The gas sensor according to claim 1, wherein the gas introduction part is formed in the diffusion resistance layer which is a porous diffusion resistance layer of the sensor element.

6. The gas sensor according to claim 5, wherein the porous diffusion resistance layer is made of alumina porous material.

7. The gas sensor according to claim 1, wherein an axial distal end portion of the inner cover is provided with an inner discharge opening.

8. A gas sensor comprising:
a sensor element for detecting a concentration of a specific gas contained in a measurement gas, the sensor element being a stacked sensor element formed by stacking an oxygen ion-conductive solid electrolyte body provided with a measurement gas-side electrode and a reference gas-side electrode, and a diffusion resistance layer which allows the measurement gas to transmit therethrough to contact with the measurement gas-side electrode;
a housing holding the sensor element inserted therein; and
an element cover disposed at an axial distal end side of the housing, wherein
the sensor element is provided with a gas introducing part for introducing the measurement gas thereinto at a distal end portion thereof, the gas introduction part being part of the diffusion resistance layer exposed to an outer surface of the sensor element,
the element cover includes an inner cover disposed so as to cover the distal end portion of the sensor element and an outer cover disposed outside the inner cover,
the outer cover is provided with an outer inlet opening for introducing the measurement gas into the outer cover,
the inner cover is provided with an inner inlet opening for introducing the measurement gas into the inner cover,
an axial intermediate position of the gas introduction part of the sensor element is more to an axial proximal end side than an axial proximal end position of the inner inlet opening of the inner cover is,
an axial distal end portion of the sensor element is more to the axial distal end side than the axial proximal end position of the inner inlet opening of the inner cover is, and
an axial distal end position of the gas introduction part of the sensor element is more to the axial proximal end side than the axial proximal end position of the inner inlet opening of the inner cover is.

9. A gas sensor comprising:
a sensor element for detecting a concentration of a specific gas contained in a measurement gas, the sensor element being a stacked sensor element formed by stacking an oxygen ion-conductive solid electrolyte body provided with a measurement gas-side electrode and a reference gas-side electrode, and a diffusion resistance layer which allows the measurement gas to transmit therethrough to contact with the measurement gas-side electrode;
a housing holding the sensor element inserted therein; and
an element cover disposed at an axial distal end side of the housing, wherein
the sensor element is provided with a gas introducing part for introducing the measurement gas thereinto at a distal end portion thereof, the gas introduction part being part of the diffusion resistance layer exposed to an outer surface of the sensor element,
the element cover includes an inner cover disposed so as to cover the distal end portion of the sensor element and an outer cover disposed outside the inner cover,
the outer cover is provided with an outer inlet opening for introducing the measurement gas into the outer cover, the inner cover is provided with an inner inlet opening for introducing the measurement gas into the inner cover, an axial middle position of the gas introduction part of the sensor element is more to an axial proximal end side than an axial proximal end position of the inner inlet opening of the inner cover is, and an axial distal end portion of the sensor element is more to the axial distal end side than the axial proximal end position of the inner inlet opening of the inner cover is.

10. The gas sensor according to claim 9, wherein an axial distal end position of the gas introduction part of the sensor element is more to the axial proximal end side than the axial proximal end position of the inner inlet opening of the inner cover is.

11. The gas sensor according to claim 9, wherein the inner cover is provided with a louver part for blocking a flow of the measurement gas to cause the measurement gas to flow to the axial proximal end side within the inner inlet opening.

12. The gas sensor according to claim 11, wherein the louver part is bent from an end portion on the axial distal end side of the inner inlet opening to inside of the inner cover, and formed so as to extend toward the axial proximal end side.

13. The gas sensor according to claim 9, wherein an axial distal end position of the outer inlet opening of the outer cover is more to the axial proximal end side than the axial proximal end position of the inner inlet opening of the inner cover is.

14. The gas sensor according to claim 9, wherein the gas introduction part is formed in the diffusion resistance layer which is a porous diffusion resistance layer of the sensor element.

15. The gas sensor according to claim 14, wherein the porous diffusion resistance layer is made of alumina porous material.

16. The gas sensor according to claim 9, wherein an axial distance between the axial middle position of the gas introduction part of the sensor element and the axial proximal end position of the inner inlet opening of the inner cover is 0 mm$<a\leq 3.0$ mm.

17. The gas sensor according to claim 9, wherein an axial distal end portion of the inner cover is provided with an inner discharge opening.

* * * * *